(12) United States Patent
Brodman et al.

(10) Patent No.: US 6,936,456 B1
(45) Date of Patent: Aug. 30, 2005

(54) BIOREMEDIATION OF NITROGENOUS CONTAMINANTS

(75) Inventors: Bruce W. Brodman, Stroudsburg, PA (US); Sheng-Yih Lee, Kearny, NJ (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 203 days.

(21) Appl. No.: 10/064,661

(22) Filed: Aug. 5, 2002

(51) Int. Cl.$^7$ .................................................. C12N 1/20
(52) U.S. Cl. ..................................................... 435/252.1
(58) Field of Search ...................................... 435/252.1

(56) References Cited

U.S. PATENT DOCUMENTS

| | | | | |
|---|---|---|---|---|
| 5,736,669 A | * | 4/1998 | Thomas et al. | 102/293 |
| 6,066,772 A | * | 5/2000 | Hater et al. | 149/124 |
| 6,274,368 B1 | * | 8/2001 | Nicklin et al. | 435/252.1 |
| 6,334,395 B1 | * | 1/2002 | Badger et al. | 435/262.5 |
| 6,668,725 B2 | * | 12/2003 | Badger et al. | 102/289 |

* cited by examiner

Primary Examiner—Herbert J. Lilling
(74) Attorney, Agent, or Firm—Robert Charles Beam; John F. Moran

(57) ABSTRACT

A novel process for the remediation of nitrogenous energetic materials such as 1,3,5,-trinitro-1,3,5-triazine (RDX) which can be used in situ on contaminated media is provided. The process comprises the bioremediation by one or more miccroorganisms capable of metabolizing the energetic materials. Examples of such microorganisms include *Rhizobium rhizogenes*, *Burkholderia* sp., and *Cladosporium cladosporioides* (ATCC 66669). Strains of these microorganisms have been deposited. The strain designated A1 has been deposited as *Rhizobium rhizogenes* BL (ATCC PTA-4110) and the strain designated C8 has been deposited as *Burkholderia* sp. (ATCC PTA-4111) Additionally, with the addition of a carbon source, such as a sugar, the process can totally degrade the energetic materials in two to three days.

4 Claims, 10 Drawing Sheets

GROWTH OF RDX-DEGRADING BACTERIA

TIME COURSE OF RDX DISAPPEARANCE

THE RDX BIODEGRADATION BY BACTERIA A1
0 DAY, RDX=50 ppm

5TH DAY, RDX NOT DETECTED AND NEW PEAK EMERGED

30TH DAY

DAY=150TH

BIOREMEDIATION OF NITROGENOUS CONTAMINANTS

FEDERAL RESEARCH STATEMENT

[The inventions herein described may be manufactured, used and licensed by or for the U.S. Government for U.S. Government purposes.]

BACKGROUND OF INVENTION

1. Field of the Invention

The present invention relates to a method for the in situ bioremediation of nitrogenous contaminants; more particularly to the use of one or more microorganisms to metabolize nitrogenous energetic materials present in a medium, such as soil and water.

2. Discussion of the Related Art

The manufacturing, use, and disposal of highly nitrogenated energetic materials have resulted in the contamination of soil and groundwater with potentially hazardous compounds. The generally high nitrogen content of such energetic materials makes the remediation of these compounds difficult and costly. Such materials include, for example, organic nitroaromatics, inorganic nitrates, organic nitramines, and organic nitrate esters. Nitramines, although apparently extremely rare in nature, are produced in significant quantities by the chemical industry and comprise, for example, an important class of energetic materials having applications as explosives and propellants. There are concerns regarding the environmental fate of nitramines due to their relative persistence and therefore there exists a need for a means of removing such contaminants from the environment without producing other undesirable pollutants.

Examples of organic nitroaromatics include TNT, hexanitrostilbene (HNS), hexanitroazobenzene (NAB), diaminotrinitrobenzene (DATB), and triaminotrinitrobenzene (TATB). Examples of organic nitramines include RDX, HMX, nitroguanidine (NQ), and 2,4,6-trinitrophenylmethylnitramine (tetryl). Examples of organic nitrate esters include PETN, nitroglycerine, and ethylene glycol dinitrate. A sample inorganic nitrate includes ammonium nitrate. RDX (1,3,5-trinitro-1,3,5-triazine is both an energetic material and a toxic substance and is currently the most important military explosive in the United States. The manufacture, handling and disposal of RDX can all lead to the contamination of the environment with RDX. The EPA has determined that RDX is a possible human carcinogen and that RDX can cause seisures in humans and animals when large amounts are inhaled or eaten. A large number of sites worldwide, including both soil and ground water, have been found to be contaiminated with RDX. These sites include manufacturing, storage, load assemble and pack, and demilitarization facilities. It has now become necessary to remediate these contaminated sites. The current method for soil remediation of RDX involves removal, incineration and replacement of the treated soil. Such a process is extremely expensive and cumbersome. Removal of RDX from ground water involves extensive and expensive filtration processes.

The use of microorganisms to remediate these sites is a potentially attractive alternative to incineration and filtration. Examples of bioremediation have been disclosed in U.S. Pat. Nos. 6,274,368 to Nicklin et al., using novel bacteria and U.S. Pat. No. 6,066,772 using a combination of anaerobic and aerobic processes. Bioremediation of energetic materials has also been described for use in ordinance the in U.S. Pat. No. 6,120,627 to Badger, et al.

The present invention provides a bioremediation process for the reduction of environmental contamination of nitrogenous energetic compounds, such as RDX.

SUMMARY OF INVENTION

The present invention is a process for remediating a contaminated medium, such as soil or water, contaminated with nitrogenous compounds. The process involves the bioremediation of a mixture comprising the contaminated medium and at least one microorganism source. Suitable microorganisms include *Rhizobium rhizogenes, Burkholderia* sp., and *Cladosporium cladosporioides*. The mixture is maintained under appropriate conditions for a period of time sufficient to yield a bioremediation product that is essentially free of the nitrogenous contaminants and their derivatives. In an alternate embodiment, a carbon source, such as a sugar, is added to the mixture to enhance the remediation process.

An additional use of the process involves incorporating the microorganisms in ordinance to provide them with self-remediating properties.

BRIEF DESCRIPTION OF DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION

Figure 1:
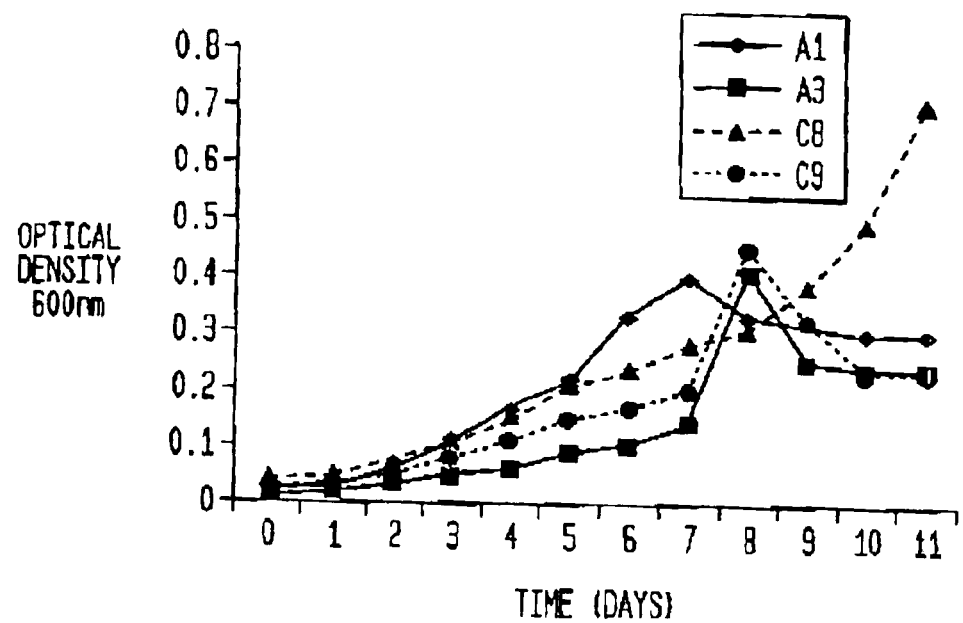
FIG. 1 shows the growth of strains A1, A3, C8, and C9 in the presence of RDX
Figure 2:
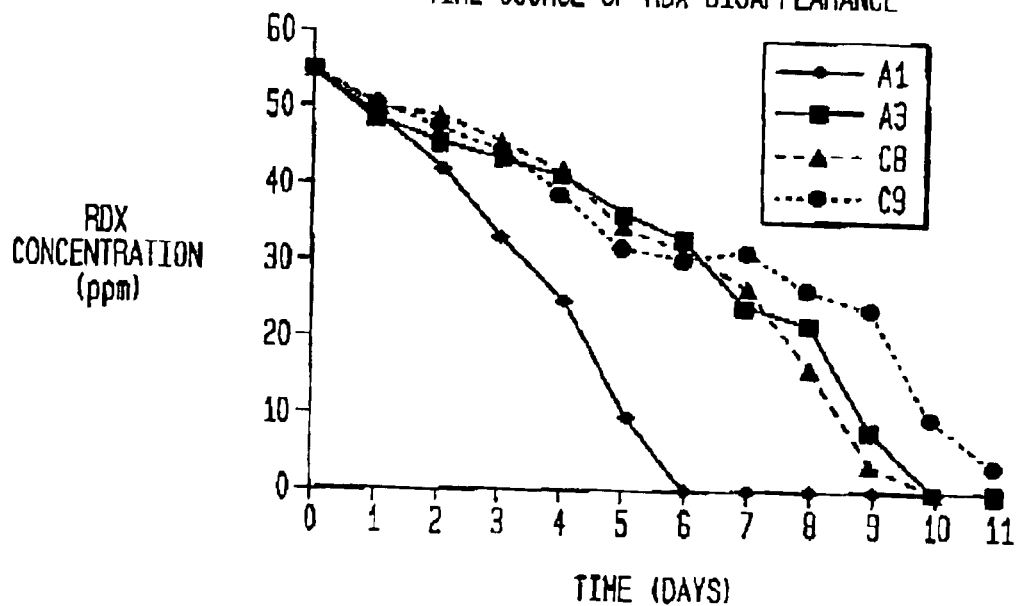
FIG. 2 shows the RDX degradation of strains A1, A3, C8, and C9.
Figure 3A:
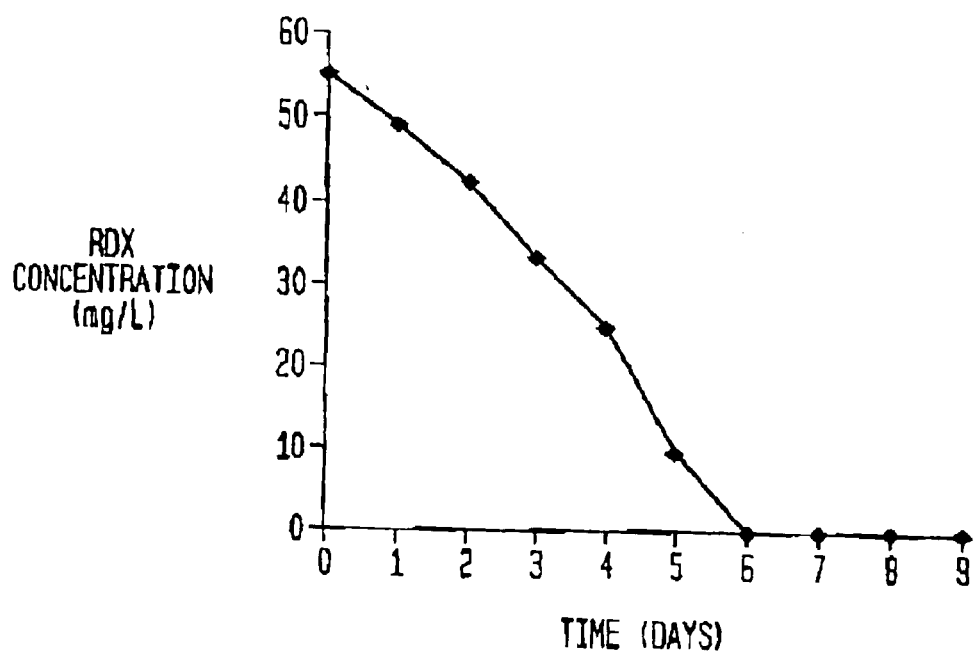
FIGS. 3A and 3B show the RDX degradation and microorganism growth of strain A1.
Figure 3B:
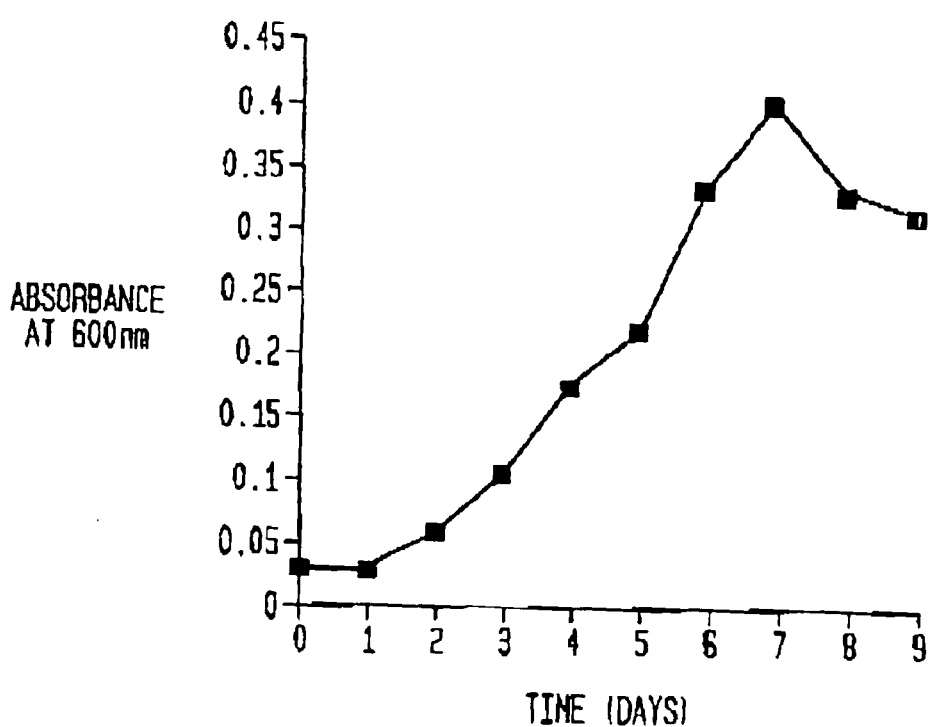
Figure 4A:
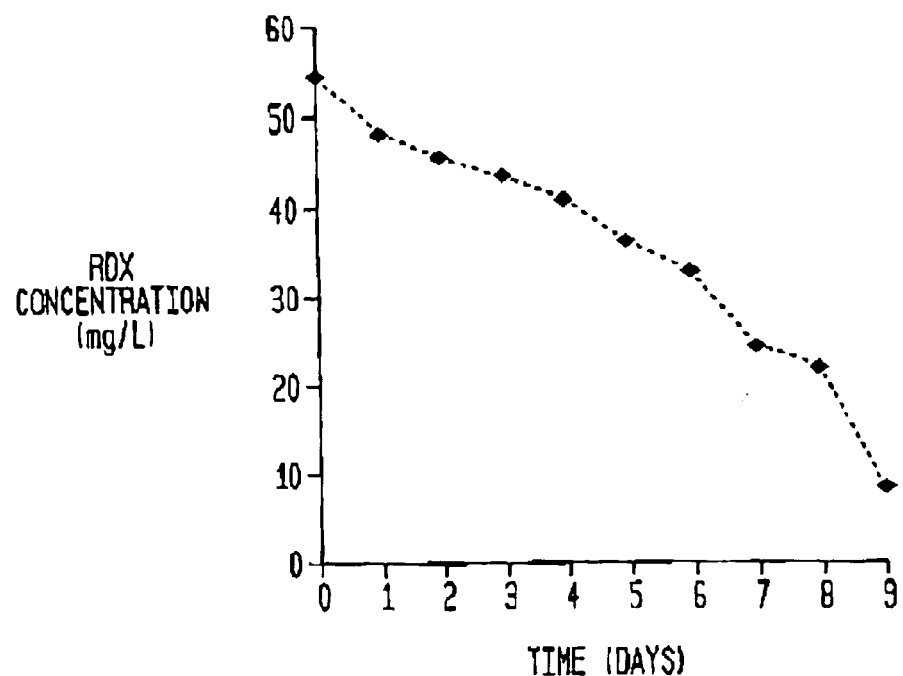
FIGS. 4A and 4B show the RDX degradation and microorganism growth of strain A3.
Figure 4B:
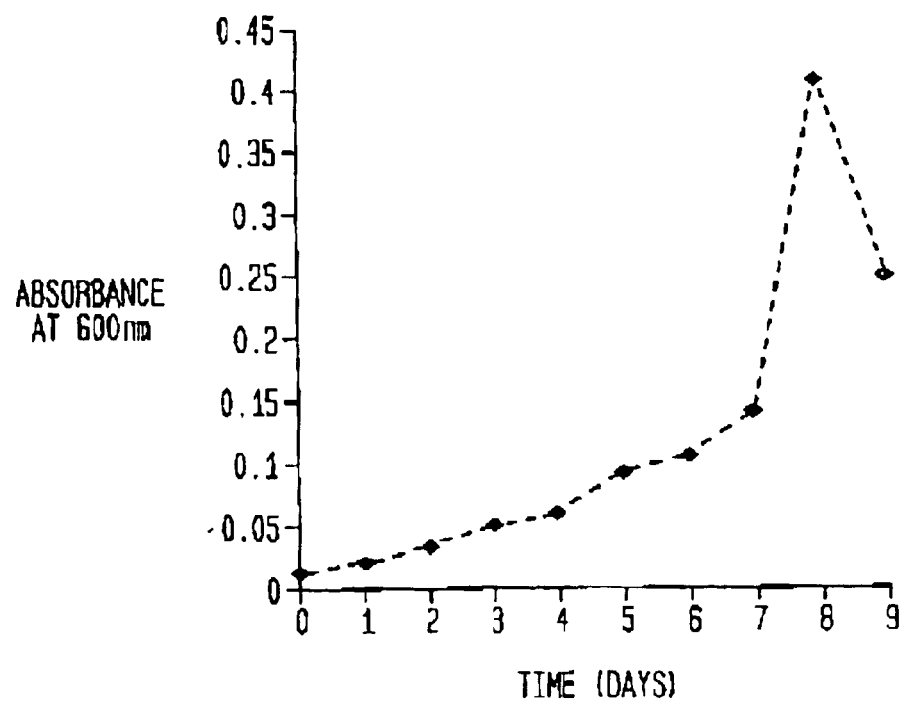
Figure 5A:
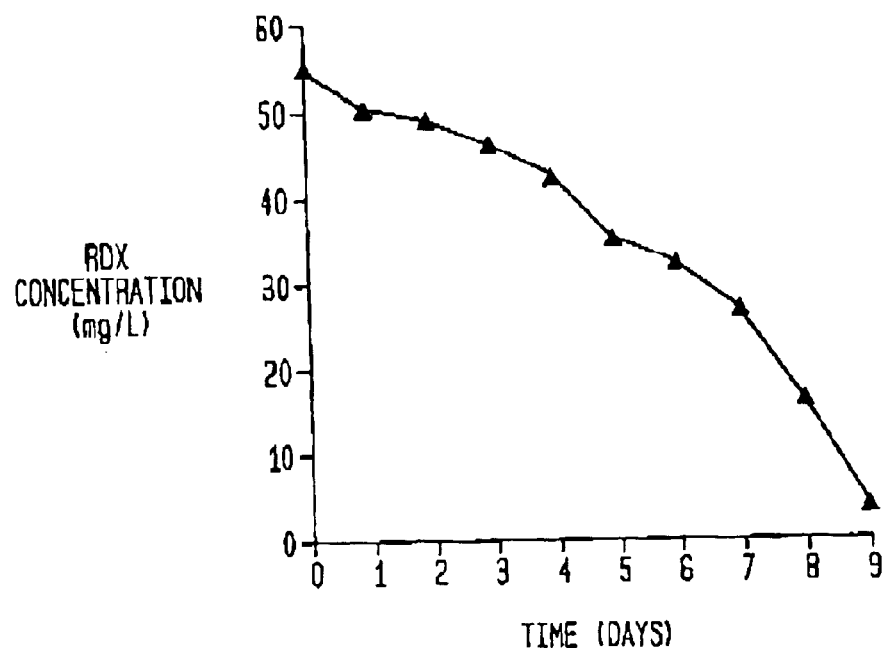
FIGS. 5A and 5B show the RDX degradation and microorganism growth of strain C8.
Figure 5B:
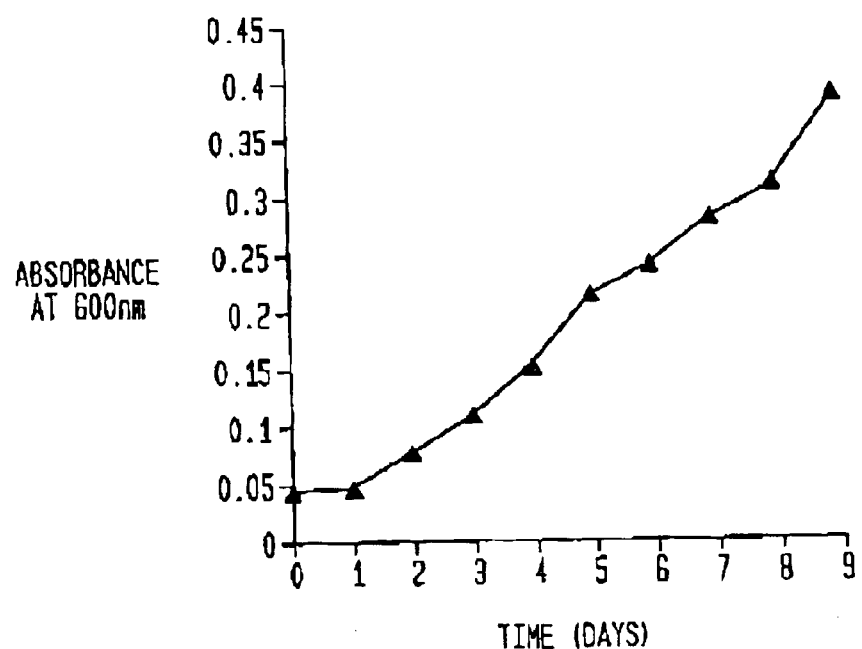
Figure 6A:
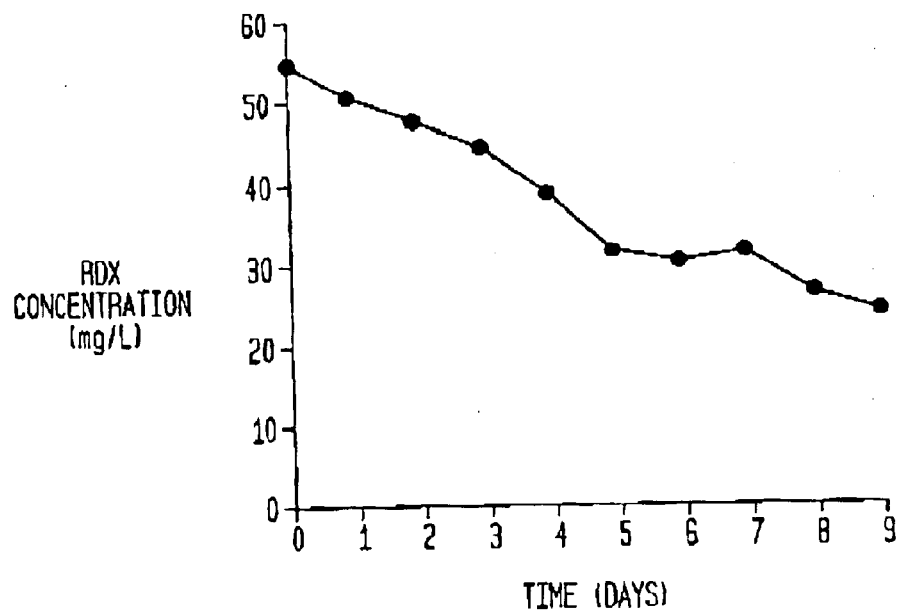
FIGS. 6A and 6B show the RDX degradation and microorganism growth of strain C9.
Figure 6B:
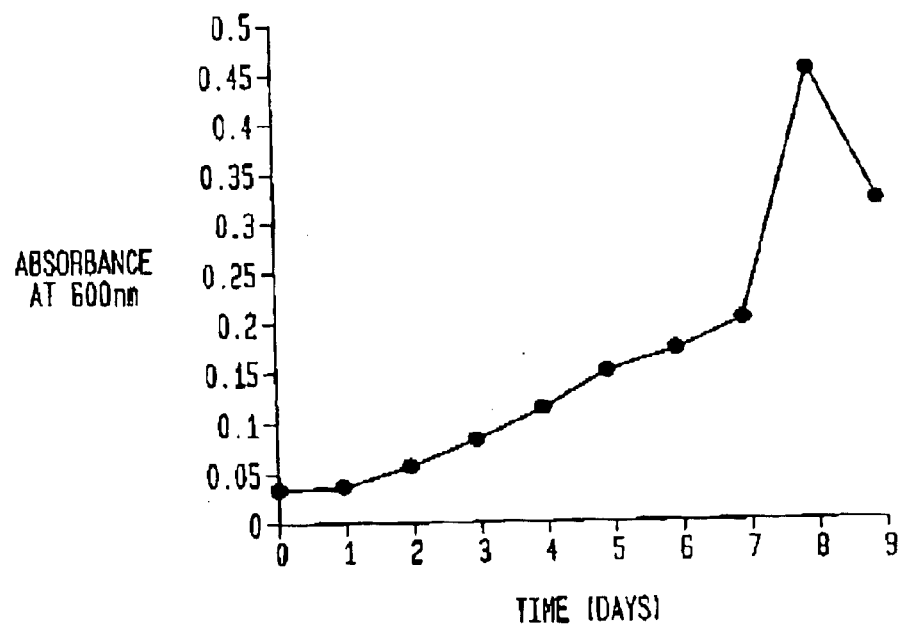

The terms "remediate" and "remediation" are used in the specification and the appended claims to refer generally to the conversion or transformation of an nitrogenous material which may be toxic and may be detonatable by shock or heat into a different chemical material which is less toxic and less explosive or non-explosive. The terms "bioremediate" and "bioremediation" are used to refer to remediation effected by the action of microorganisms. The present invention is thus one intended to bioremediate these nitrogenous material-sKnown energetic materials, which may be bioremediated, include materials that are classified as organic nitroaromatics, inorganic nitrates, organic nitramines, or organic nitrate esters. Examples of organic nitroaromatics include TNT, hexanitrostilbene (HNS), hexanitroazobenzene (NAB), diaminotrinitrobenzene (DATB), and triaminotrinitrobenzene (TATB). Examples of organic nitramines include RDX, HMX, nitroguanidine (NQ), and 2,4,6-trinitrophenylmethylnitramine (tetryl). Examples of organic nitrate esters include PETN, nitroglycerine, and ethylene glycol dinitrate. A suitable inorganic nitrate includes ammonium nitrate. A number of new microorganisms within the scope of the present invention were deposited on Mar. 13, 2002, with the American Type Culture Collection (hereinafter "ATCC") in accordance with provisions of the Budapest Treaty on the International Recognition of the Deposit Microorganisms for the Purpose of Patent Procedure. The ATCC is located at 10801 University Boulevard, Manassas, Va. 20110-2209 U.S.A. The deposited microorganisms have been assigned ATCC Designation Nos. PTA-4110, PTA-4111 and ATCC 66669. For purposes of this disclosure, the microorganisms deposited with the ATCC and the ATCC Designation Nos. PTA-4110, PTA-4111 and ATCC 66669 are hereby incorporated by reference. These microorganisms were identified by the Deutsche Sammlung von Mikroorganismen und Zellkulturen GmbH, and the results of their report are shown in Tables I and II.

TABLE I

Properties of the Strain

| | |
|---|---|
| Shape of cells | rods |
| width μm | 0.7–0.9 |
| length μm | 1.5–3.5 |
| Pigments | – |
| Flagella | + |
| Gram reaction | – |
| Lysis by 3% KOH | + |
| Aminopeptidase (Cerny) | + |
| Catalase activity | + |
| Oxidase activity | + |
| ADH | – |
| Hydrolysis of gelatin | – |
| esculin | – |
| casein | – |
| starch | + |
| DNA | + |
| NO$_2$ from NO$_3$ (24$^{th}$) | – |
| Denitrification | – |
| Utilization of | + |
| m-hydrox-benzoat | |
| α-amylamin | + |

TABLE I-continued

Properties of the Strain

| | |
|---|---|
| glucose | + |
| citrat | + |
| malat | + |
| arabinosse | + |
| mannose | + |
| mannit | + |
| adipat | – |
| caprat | + |
| gluconat | + |
| maltose | – |
| citraconat | – |
| itaconat | + |
| inositol | + |
| mesaconat | + |
| butandiol | – |
| tryptamin | – |
| butylamin | – |
| L-arabitol | – |
| rhamnose | + |
| L-alanin | + |
| melibiose | – |

Result:=*Burkholderia* sp.

The partial sequencing of the 16SrDNA shows a similarity of around 97% to several species of the genus *Burkholderia*.

The profile of the cellular fatty acids is typical for the *Burkholderia*-group.

The results of the physiological tests do not allow a complete identification of this strain. They point to *B. cepacia*.

Considering all these results, especially the result of the partial sequencing, this strain may be a member of a new species within this genus.

TABLE II

Fatty Acid Profile

| RT | Area | Ar/Ht | Respon | ECL | Name | % | Comment 1 | Comment 2 |
|---|---|---|---|---|---|---|---|---|
| 1.766 | 308111640 | 0.037 | | 7.000 | SOLVENT PEAK | | <min rt | |
| 2.060 | 755 | 0.035 | | 7.551 | | | <min rt | |
| 4.046 | 600 | 0.036 | 1.077 | 10.925 | Sum in Feature 2 | 0.17 | ECL deviates –0.003 | unknown 10.928 |
| 6.183 | 1486 | 0.045 | 1.012 | 12.937 | 13:1 AT 12-13 | 0.40 | ECL deviates 0.001 | |
| 7.663 | 13906 | 0.040 | 0.988 | 14.001 | 14:0 | 3.65 | ECL deviates 0.001 | Reference –0.004 |
| 9.015 | 1607 | 0.067 | 0.973 | 14.861 | 15:1 w6c | 0.42 | ECL deviates 0.005 | |
| 9.231 | 1415 | 0.067 | 0.971 | 14.998 | 15:0 | 0.37 | ECL deviates –0.002 | Reference –0.007 |
| 10.061 | 18511 | 0.045 | 0.965 | 15.490 | Sum in Feature 2 | 4.75 | ECL deviates 0.002 | 14:0 3OH/16:1 ISO I |
| 10.620 | 80640 | 0.045 | 0.960 | 15.821 | Sum in Feature 3 | 20.60 | ECL deviates –0.001 | 16:1 w7c/15 iso 2OH |
| 10.924 | 77418 | 0.046 | 0.958 | 16.001 | 16:0 | 19.73 | ECL deviates 0.001 | Reference –0.005 |
| 12.479 | 6477 | 0.051 | 0.950 | 16.889 | 17:0 CYCLO | 1.64 | ECL deviates 0.001 | Reference –0.004 |
| 12.672 | 932 | 0.047 | 0.949 | 17.000 | 17:0 | 0.24 | ECL deviates –0.000 | Reference –0.006 |
| 12.762 | 3488 | 0.051 | 0.949 | 17.051 | 16:1 2OH | 0.88 | ECL deviates 0.003 | |

TABLE II-continued

Fatty Acid Profile

| RT | Area Ar/Ht | Respon | ECL | Name | % | Comment 1 | Comment 2 |
|---|---|---|---|---|---|---|---|
| 13.089 | 4209 0.050 | 0.947 | 17.235 | 16:0 2OH | 1.06 | ECL deviates 0.002 | |
| 13.592 | 14423 0.049 | 0.945 | 17.520 | 16:0 3OH | 3.62 | ECL deviates 0.001 | |
| 14.136 | 154907 0.048 | 0.943 | 17.827 | 18:1 w7c | 38.84 | ECL deviates 0.004 | |
| 14.440 | 3834 0.047 | 0.942 | 17.998 | 18:0 | 0.96 | ECL deviates −0.002 | Reference −0.006 |
| 14.586 | 833 0.052 | 0.941 | 18.081 | 11 methyl 18:1 w7c | 0.21 | ECL deviates −0.000 | |
| 16.033 | 6740 0.051 | 0.936 | 18.903 | 19:0 CYCLO w8c | 1.68 | ECL deviates 0.001 | Reference −0.003 |
| 16.362 | 2275 0.060 | 0.935 | 19.090 | 18:1 2OH | 0.57 | ECL deviates 0.001 | |
| 17.655 | 948 0.086 | 0.931 | 19.834 | 20:1 w7c | 0.23 | ECL deviates 0.003 | |
| ****** | 19111 | | | Summed Feature 2 | 4.92 | 12:0 ALDE? | unknown 10.928 |
| ****** | | | | | | 16:1 ISO 1/14:0 3OH | 14:0 3OH/16:1 ISO I |
| ****** | 80640 | | | Summed Feature 3 | 20.60 | 16:1 w7c/15 iso 2OH | 15:0 ISO 2OH/16:1w7c |

| Solvent Ar | Total Area | Named Area | % Named | Total Amnt | Nbr Ref | ECL Deviation | Ref ECL Shift |
|---|---|---|---|---|---|---|---|
| 308111640 | 394649 | 394649 | 100.00 | 376057 | 7 | 0.002 | 0.005 |

| TSBA40 [Rev 4.10] | Burkholderia | 0.869 (*Pseudomonas cepacia*) |
|---|---|---|
| | B. cepacia | 0.869 (*Pseudomonas cepacia*) |
| | B, c, GC subgroup B* | 0.869 (*Pseudomonas cepacia*) |
| | B, c, GC subgroup A* | 0.514 (*Pseudomonas cepacia*) |
| | B. pyrrocinia** | 0.639 (*Pseudomonas pyrrocinia*) |
| | B. glathei** | 0.624 (*Pseudomonas glathei*) |

The microorganisms deposited with the ATCC where isolated from RDX contaminated soil. The isolated microorganisms demonstrated the ability to metabolize and degrade energetic materials in a way that contribute to the detoxification and neutralization of the energetic material. It was subsequently found that all of the organisms could degrade RDX and that at least two of the isolated microorganisms could, with the addition of an oxidizable carbon source, such as glucose, totally degrade RDX in a matter of two to three days. It is now possible to utilize these organisms to accomplish a variety of functions—both soil and groundwater in situ bioremediation can be accomplished using these organisms providing a much more economical and more environmentally friendly method. The same organisms can be used, for example, to treat manufacturing waste or to incorporate into self-remediating ordinance.

In one preferred embodiment of the present invention, the microorganisms are selected from the group comprising *Rhizobium rhizogenes, Burkholderia* sp., and *Cladosporium cladosporioides*. Any microorganisms other than the microorganisms Identified above are considered to be within the scope of the invention disclosed herein, provided that such microorganisms perform any of the functions described above having utility in the remediating of a nitrogenous energetic material. Correspondingly, any microorganism is considered to be within the scope of the invention disclosed herein, provided the microorganism exhibits any utility relative to the bioremediating of nitrogenous energetic materials.

In another preferred embodiment of the process of this invention a medium, for example soil or water, containing nitrogenous contaminants is mixed with a microorganism source. In an alternative embodiment, the process of this invention may be used to convert hazardous contaminants into non-hazardous metabolites by mixing contaminants with contaminated or uncontaminated medium (e.g., soil or water) to provide a contaminated medium and thereafter remediating the mixture according to the process of this invention.

The process of this invention is useful for remediating contaminated soil or water containing high concentrations of contaminants. For example, microorganisms of the present invention were isolated from contaminated soil having at least 7000 parts per million by weight of contaminants. Theoretically there should be no upper limit for the concentration of contaminants. There may be an effect on the rate of bioremediation related to the limits of solubility of the contaminants. For example, with an RDX solubility in water of about 60 ppm, it is preferred that an RDX contaminated medium contain less than about 60 parts per million by weight of RDX. If necessary, uncontaminated medium may be admixed with contaminated medium to reduce the concentration of contaminants in the medium used to a desired concentration before bioremediation.

The term "microorganism" refers to any existing microorganisms including, for example, bacteria, protozoa, fungi, and mixtures thereof. Sources of useful naturally occurring microorganisms include, but are not limited to, soil, animal manures such as cow and horse manure, anaerobic digester sludge, aerobic digester sludge, sewage sludge and mixtures thereof. A microorganism source can also be a cultured microorganism.

In another preferred embodiment an additional ingredient is added to the bioremediation mixture to provide an oxidizable carbon source. The carbon source may be any material that includes purified or naturally occurring carbohydrates such as glucose, sucrose, fructose or other sugars, glycerol, and starches derived from or contained in agricultural products. Examples of useful carbon sources include dextrose, molasses, beet juice, potatoes, sweet potatoes, cornstarch, potato starch, and mixtures thereof. It is preferred that the carbon source is a water-soluble carbohydrate such as sucrose or dextrose. The carbon source should be incorporated into the bioremediation mixture in an amount ranging from about 0.1% to about 10% by weight, preferably in an amount less than 6% by weight, more preferably ranging from about 0.2% to about 0.4% by weight.

The ingredients used in the bioremediation mixture may be combined by any method known in the art for combining solid materials in the case of a soil medium or liquids in the case of an aqueous medium. For example, solid materials may be combined using a backhoe, bulldozer, or batch mixer.

The bioremediation occurs for a period of time sufficient to decrease the concentrations of contaminants and their reduced derivatives to concentrations below the accepted standards for the proposed use of the treated product. Generally the bioremediation mixture will be maintained at aerobic conditions for a period of time ranging from about 1 day to about 60 days or more. When a carbon source is added to the mixture, the process can be completed in less than about 10 days, an even as quickly as about 2 to 3 days.

The process of this invention effectively reduces the weight amounts of contaminants in contaminated mediums below the level required for the soil or water to be used for both site specific restricted uses and to be used for unrestricted uses. In order for the remediated medium to be used for site specific restricted uses, the weight of contaminants in the remediated medium generally should not exceed the following amounts for example: TNT-480 ppm; RDX-40 ppm; HMX-33,000 ppm; Tetryl-6500 ppm; 2,4DNT-1300 ppm; and 2,6DNT-650 ppm. In order for the remediated medium produced by the process of this invention to be used for unrestricted uses, the contaminants found in the remediated medium should generally not exceed the following values for example: TNT-48 ppm; RDX-4 ppm; HMX-3,300 ppm; tetryl-650 ppm; 24DNT-130 ppm; and 2,6DNT-65 ppm. The length of time that the processes of this invention must be operated in order to produce a restricted medium or unrestricted medium will vary depending primarily upon the amount of contaminants found in the contaminated medium. Typically the process of this invention will reduce the amount of contaminants in a contaminated medium by at least 99.99% when the medium includes about 1 or less mg per kg of contaminants. The weight percent contaminant reduction will increase with increasing weight amount of contaminants in the contaminated medium. Once the bioremediation process is complete, the medium may be used as deemed appropriate by regulatory authorities.

The following examples are provided to further illustrate the invention and are not limitations on the scope of the present invention, the scope of the invention being limited by the attached claims.

EXAMPLESIsolation of microorganisms The microorganisms were isolated using techniques standard in the art, from samples collected from a natural source containing RDX as the nitrogen source.

Soil samples were obtained from 3 sites (site A, B & C) having over 300 of bacterial colonies cultured on minimal salt medium (MSM) agar with 50 ppm RDX. The minimal salt medium was comprised of: 2 g Glucose, 0.8 of $K_2HPO_4$, 0.2 g of $KH_2PO_4$, 0.2 g of $MgSO_4 0.7H_2O$, 0.1 g of $CaCl_2.2H_2O$, 0.1 g of NaCl, 0.01 g of $FeSO_4 0.7H_2O$ and 1 ml trace elements (per liter) were mixed. To the mixture was added 15g agar per liter before autoclaving. RDX was the only nitrogen source, no other nitrogen source was added.

Only bacteria from Sites A and C exhibited RDX degradation. Four (4) bacterial strains exhibiting RDX degradation were isolated and designated as bacteria A1, A3, C8 and C9. (All preliminary Isolation from site B failed to grow in minimal salt medium liquid). At least one fungus exhibiting RDX degradation was isolated and designated as F1.

Figure 8:
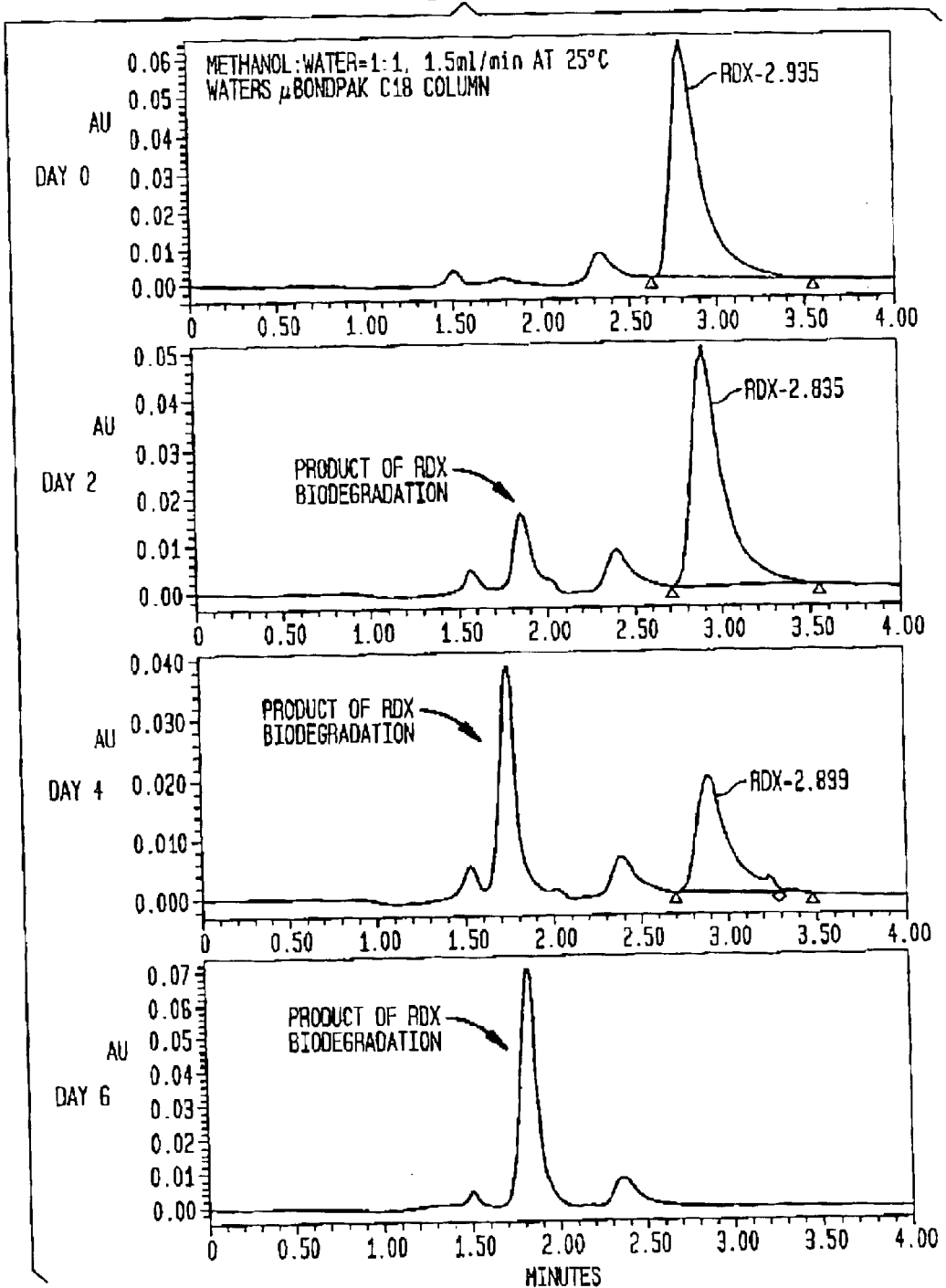
FIG. 8 shows HPLC analysis of RDX biodegradation of strain A1.
Figure 9:
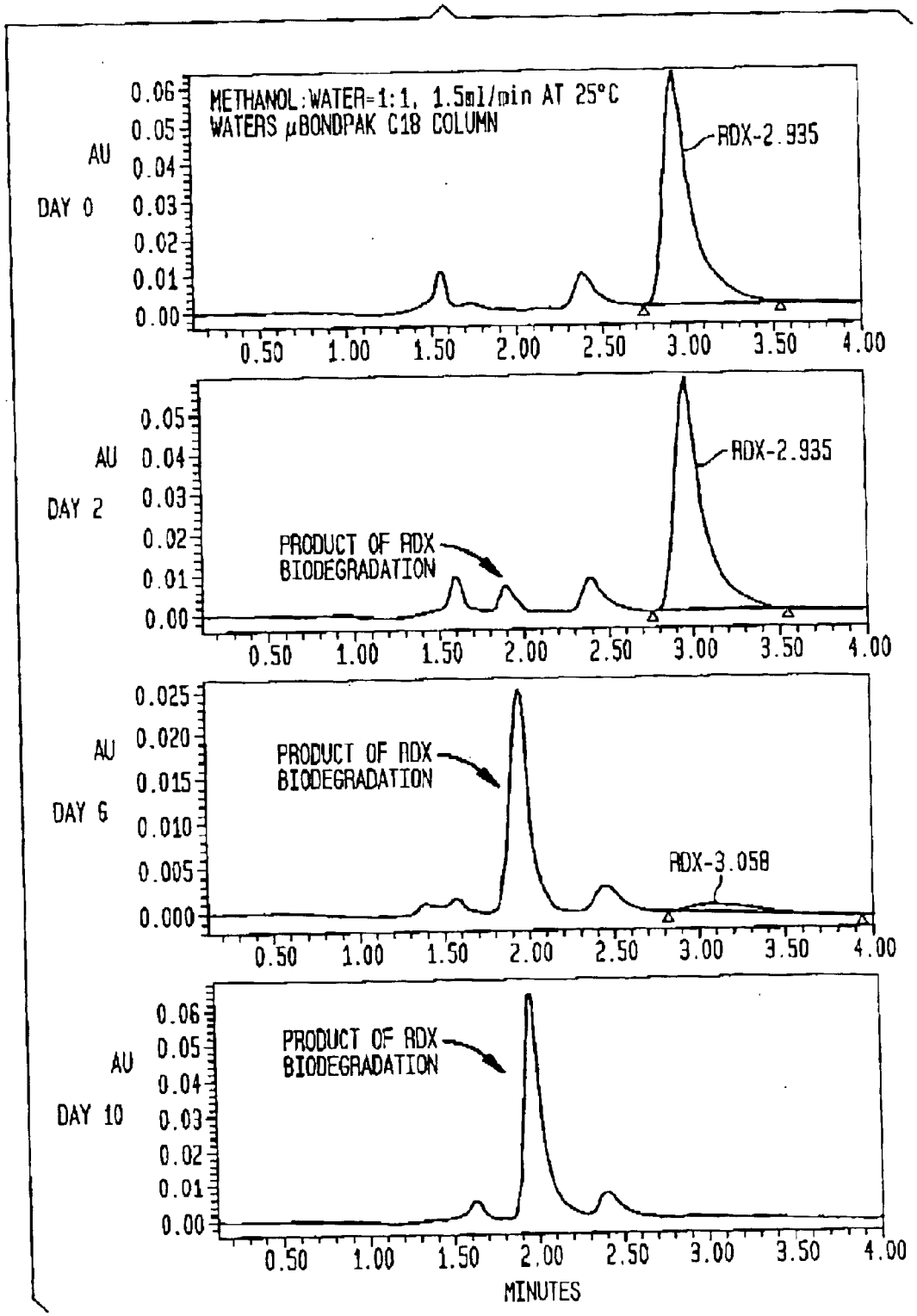
FIG. 9 shows HPLC analysis of RDX biodegradation of strain C8.
Figure 10:
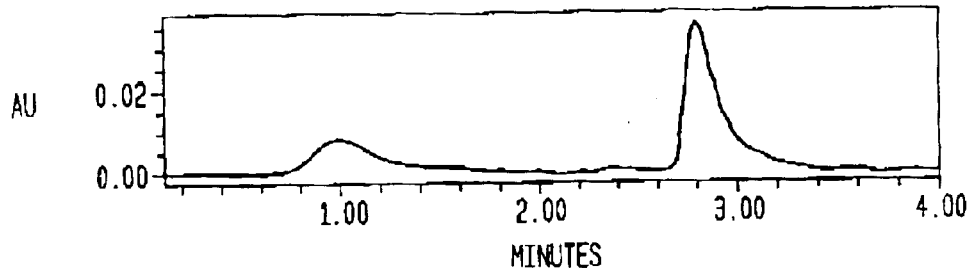
FIG. 10 shows HPLC analysis of long-term RDX degradation of strain A1.
Figure 10:
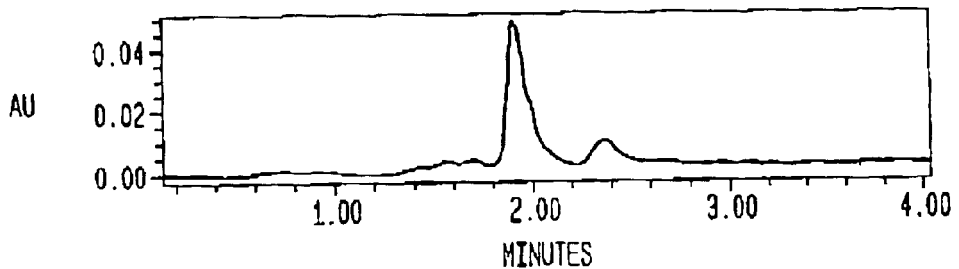
Figure 10:
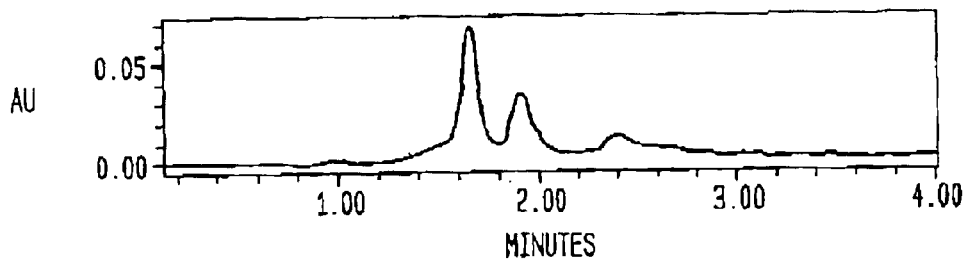
Figure 10:
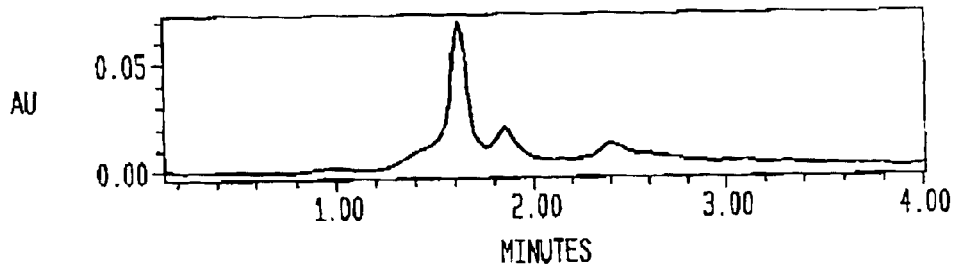
Figure 11:
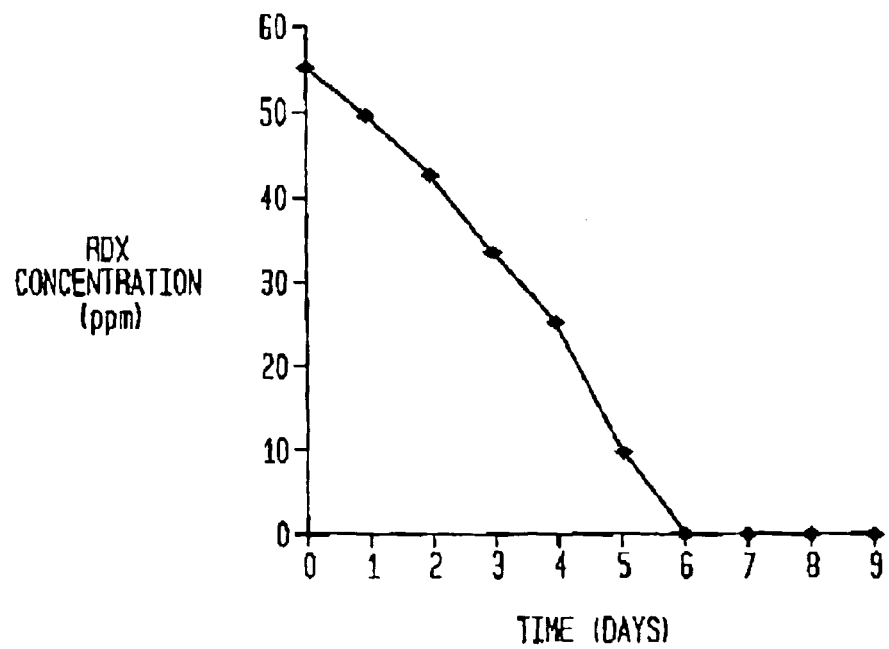
FIG. 11 shows RDX degradation of microorganism A1 with a carbon source.

The bacteria A1, A3, C8, and C9 were isolated and incubated on MSM agar with 55 ppm RDX. After 24 hours of incubation, each bacteria culture exhibited two possible RDX metabolites as shown by HPLC. One of these two new peak (metabolites) is a minor product (peak) that was detected earlier (over 12 hrs) before the second major peak. However, occasionally this "minor" new peak was also observed in the all-new medium without any bacterial culture added. FIGS. 8 and 9 show the RDX and metabolite peaks from HPLC for strain A1 and C8 respectively.

High purity RDX was obtained from Chem Service Inc. (West Chester, Pa.) and other chemicals were of analytical grade, and unless stated otherwise, were obtained from Fischer Scientific (Springfield, N.J.).

HPLC Column Tests

All 4 major types of HPLC Columns (Silica, Phenyl, C18, C8) from major manufacturers (HP, Aligent, Waters, Supleco, MetaChem, Restek and Alltech) have been thoroughly tested for these two new metabolite peaks. Two of 32 HPLC columns separated these peaks as "acceptable" (Waters Nova Using HPLC, Time Course measurements of RDX biodegradation were repeated three times for each microorganism. FIGS. 3A–B, 4A–B, 5A–b and 6A–B illustrate the Time Course measurements of RDX degradation and bacteria growth over a nine (9) day period for bacteria A1, A3, C8, and C9 respectively. The fractions of possible RDX metabolites were also collected.

Anaerobic Growth pH Tests

Figure 7:
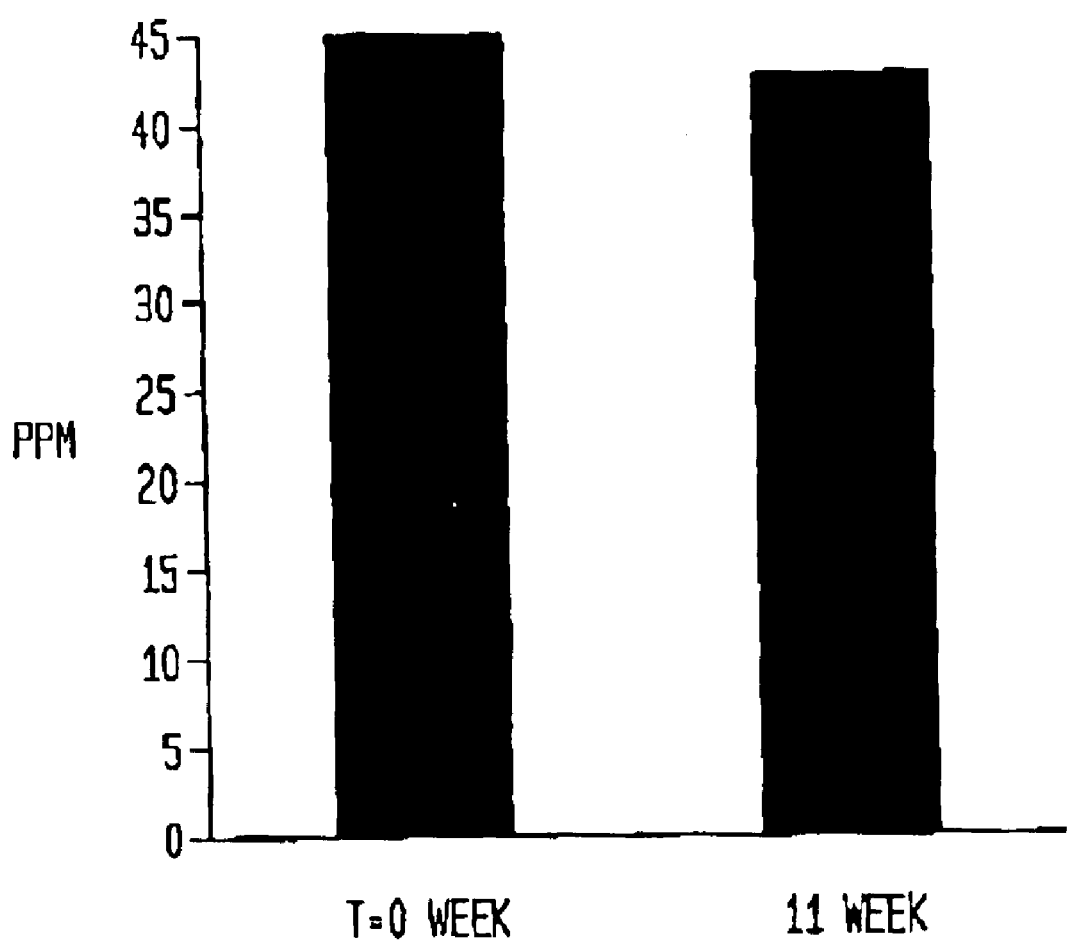
FIG. 7 shows long-term incubation of strain A1.

Long Term Incubation FIG. 7 shows RDX biodegradation for 11-week incubation of A1 growing in MSM without agar.

Growth with an Oxidizable Carbon Source

Figure 12:
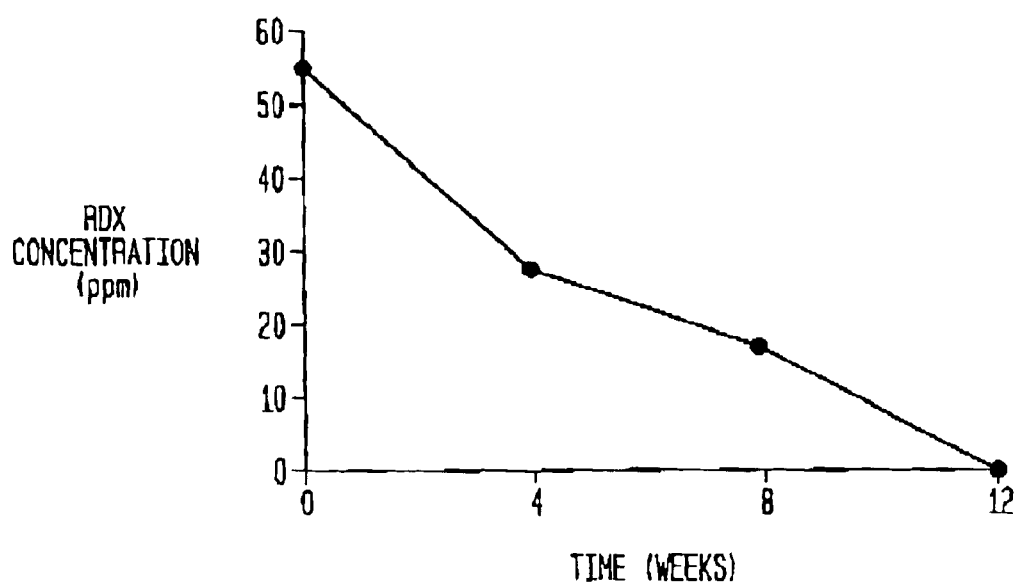
FIG. 12 shows RDX degradation of microorganism F1 with a carbon source.

FIG. 12 shows the time course for bioremediation of RDX by *Cladosporium cladosporioides* (ATCC 66669)OLE-LINK1 in minimal salt medium with a carbon source supplement (glucose: 2 g per liter). TOLE_LINK1otal RDX disappeared after 12-week incubation. Data points represent duplicate cultures. Formaldehyde, nitrite and nitrate were also detected in culture media during the course of experiment which indicated complete RDX degradation.

Thus according to the invention there is provided a *Burkholderia* sp., bacterial strain referred to as C8 and deposited as ATCC PTA-4111, and mutants and variants thereof, capable of degrading RDX Gram stain—Shape of Cells Rods Size (Width×Length, µm) 0.7–0.9×1.5–3.5 Motility (Flagella)+Catalase+Oxidase+Thus according to the invention there is provided a *Cladosporium cladosporioides* fungal strain referred to as F1 and deposited as ATCC 66669, and mutants and variants thereof, capable of degrading RDX Gram stain fungusno Gram stain Mycelium olive-green color Colony growth 1 mm per day on maltextract agar at 25° C. Terminal condia ovoid shape and smooth-walled (size 3 to 7×3 µm) Conidiphores warty and brownish with treelike branching Growth at 37° C.—Instead of the precise starting organism deposited, a mutant thereof, e.g. derived by gamma-ray irradiation or the use of a chemical mutant, induction by culture on another medium etc. or a transconjugant thereof with another bacterium or an artificially produced variant can be used. The ability of any such organism to give the remediation activity can be readily determined by the skilled person.

According to the present invention, the method comprises the step of inoculating the contaminated environment/medium with a sample of the microorganism isolate of A1, A3, C8, C9, F1, or a combination thereof and allowing the microorganism to consume the nitrogenous contaminant present in the environment/medium. The environment/medium may be, for example, a contaminated ground water aquifer, a waste stream of material containing contaminant, a sample of contaminated earth or other material. The bioremediation treatment may be conveniently carried out in a reactor vessel or in situ, by introducing the isolate directly into the environment by inoculating the contaminated medium (soil or water) with it. Other appropriate methods of effecting treatment will be readily apparent to those skilled in the art.

In another embodiment, the microorganisms are incorporated in self-destruct mechanisms for devices such as unexploded ordinance including old land mines, unexploded bombs, and misfired or unexploded missiles and rockets. In one embodiment of such a device microencapsulated microorganisms are incorporated into energetic compositions during manufacturing, wherein the capsule wall material is made from a water-soluble material. If the item did not function properly then atmospheric moisture would free the organisms and start the degradation process. Thus, resulting in rendering the ordinance item safe. Examples of suitable micro encapsulation materials include: sugars, such as glucose; gelatin, alginate, and other materials known in the art. Micro encapsulation of microorganisms is accomplished by techniques known in the art.

Another embodiment comprises a dissolving barrier between a reservoir of microorganisms and the energetic material, which is water soluble or slowly self-effacing in the presence of water, an aqueous solution or microorganisms. Such self-effacing barriers eventually degrade and release the microorganisms to remediate the energetic material. Examples of materials that can be utilized as self-effacing barriers include sugars, gelatin, alginate, starch, and acrylamide. The barriers can be formulated and designed to provide precisely timed effacing and microorganism release.

Alternate embodiments include such devices wherein microorganisms are intermixed in the energetic material or are disposed adjacent to an exterior surface of the energetic material so that the microorganisms are in proximity to said energetic material and can initiate bioremediation of the energetic material when the microorganisms are released and mobile. In yet another embodiment the microorganism can be incorporated in a distinct bioremediation apparatus that is coupled to a corresponding device.

The microorganism intermixed in the energetic material can be in aggregations or clusters such as pellets, capsules, or shards. The microorganisms disposed against an exterior surface of the energetic material can be in the form of a powder of microorganisms dispersed on the top surface of the energetic material.

What is claimed is:

1. A biologically pure culture of one or more microorganisms, and mutants thereof having all of the identifying characteristics of said microorganisms, wherein said microorganisms are capable of degrading nitrogenous material said microorganisms being selected from the group consisting of, *Rhizobium rhizogenes* (ATCC PTA-4110), *Burkholderia* sp. (ATCC PTA-4111), *Cladosporium cladosporiodes* (ATCC 66669), and mixtures thereof.

2. The culture of claim 1 wherein said nitrogenous material is 1,3,5-trinitro-1,3,5-triazine (RDX).

3. The culture claim 1 wherein said microorganism is *Burkholderia* sp. (ATCC PTA-4111).

4. A biologically pure culture of *Burkholderia* sp. (ATCC PTA-4111), and mutants thereof having all of the identifying characteristics of said strain, wherein said strain is capable of degrading 1,3,5-trinitro-1,3,5-triazine (RDX).

* * * * *